United States Patent
Gifford et al.

(10) Patent No.: US 9,737,073 B2
(45) Date of Patent: Aug. 22, 2017

(54) HERBICIDAL WEED CONTROL FROM COMBINATIONS OF FLUROXYPYR AND ALS INHIBITORS

(71) Applicant: Dow AgroSciences LLC, Indianapolis, IN (US)

(72) Inventors: James M. Gifford, Lebanon, IN (US); Richard K. Mann, Franklin, IN (US); Ändrea C. McVeigh-Nelson, Indianapolis, IN (US); David G. Ouse, Indianapolis, IN (US); Christopher J. Voglewede, Calgary (CA)

(73) Assignee: Dow AgroSciences LLC, Indianapolis, IN (US)

(*) Notice: Subject to any disclaimer, the term of this patent is extended or adjusted under 35 U.S.C. 154(b) by 69 days.

(21) Appl. No.: 14/734,686

(22) Filed: Jun. 9, 2015

(65) Prior Publication Data
US 2015/0351395 A1    Dec. 10, 2015

Related U.S. Application Data

(60) Provisional application No. 62/009,717, filed on Jun. 9, 2014.

(51) Int. Cl.
 *A01N 25/00* (2006.01)
 *A01N 43/54* (2006.01)
 *A01N 43/707* (2006.01)
 *A01N 43/40* (2006.01)
 *A01N 43/90* (2006.01)

(52) U.S. Cl.
 CPC ............ *A01N 43/40* (2013.01); *A01N 43/90* (2013.01)

(58) Field of Classification Search
None
See application file for complete search history.

(56) References Cited

U.S. PATENT DOCUMENTS

| 2011/0098181 A1 | 4/2011 | Mann et al. |
| 2011/0098182 A1 | 4/2011 | Mann et al. |
| 2013/0143739 A1* | 6/2013 | Ovalle ............... A01N 43/40 504/105 |
| 2013/0157852 A1 | 6/2013 | Mann |
| 2014/0094366 A1 | 4/2014 | Mann et al. |
| 2015/0173364 A1* | 6/2015 | Caceres ............... A01N 43/84 504/130 |

FOREIGN PATENT DOCUMENTS

| AU | 646560 B2 | 2/1994 |
| CN | 101530105 A | 9/2009 |
| CN | 102726400 A | 10/2012 |

OTHER PUBLICATIONS

International Search Report and Written Opinion of the International Searching Authority from Application No. PCT/US2015/034893, mailed Oct. 19, 2015, 15 pages.

* cited by examiner

*Primary Examiner* — Alton Pryor
(74) *Attorney, Agent, or Firm* — Michael J. Terapane; Meunier Carlin & Curfman, LLC

(57) ABSTRACT

Provided herein are herbicidal compositions containing of (a) fluroxypyr or an agriculturally acceptable ester or salt thereof and (b) an ALS-inhibiting herbicide, wherein the ALS-inhibiting herbicide is diclosulam, cloransulam, chlorimuron, or thifensulfuron, or an agriculturally acceptable ester or salt thereof. The compositions provide synergistic weed control of undesirable vegetation in areas including, but not limited to, soybean, cotton, corn, sorghum, sunflower, sugarcane, sugar beets, alfalfa, cereals (including but not limited to wheat, barley, rice and oats), non-crop, fallow-bed, perennial crop, fruiting crop, or plantation crop areas.

51 Claims, No Drawings

HERBICIDAL WEED CONTROL FROM COMBINATIONS OF FLUROXYPYR AND ALS INHIBITORS

CROSS REFERENCE TO RELATED APPLICATIONS

This application claims the benefit of U.S. Provisional Patent Application Ser. No. 62/009,717 filed Jun. 9, 2014, which is expressly incorporated by reference herein.

BACKGROUND

The protection of crops from weeds and other vegetation which inhibit crop growth is a constantly recurring problem in agriculture. Thus, there remains a need for compositions and methods that are effective in controlling undesirable vegetation.

SUMMARY

Herbicidal compositions containing synergistically effective amounts of (a) fluroxypyr or an agriculturally acceptable ester or salt thereof and (b) an acetolactate synthase (ALS)-inhibiting herbicide including, but not limited to, diclosulam, cloransulam, chlorimuron, and thifensulfuron, or an agriculturally acceptable ester or salt thereof, are described herein.

Methods of controlling undesirable vegetation that include contacting the undesirable vegetation or the locus thereof with herbicidally effective amounts of: (a) fluroxypyr or an agriculturally acceptable ester or salt thereof and (b) an ALS-inhibitor herbicide including, but not limited to, diclosulam, cloransulam, chlorimuron, and thifensulfuron, or an agriculturally acceptable ester or salt thereof, are also described herein.

The undesirable vegetation may include herbicide resistant or tolerant weeds, including those occurring in soybean, sunflower, sugar beet, canola, oilseed rape, cotton, corn, sorghum, cereals (including but not limited to wheat, barley, rice, and oats), non-crop, fallow-bed, perennial crop, fruiting crop, or plantation crop areas.

DETAILED DESCRIPTION

I. Definitions

The term "herbicide", as used herein, means an active ingredient that kills, controls or otherwise adversely modifies the growth of plants. As used herein, a "herbicidally effective or vegetation controlling amount" is an amount of active ingredient which causes a "herbicidal effect,". i.e. an adversely modifying effect and includes deviations from natural development, killing, regulation, desiccation, retardation.

As used herein, controlling undesirable vegetation means preventing, reducing, killing, or otherwise adversely modifying the development of plants and vegetation.

As used herein, "plants" and "vegetation" include, but are not limited to, germinant seeds, emerging seedlings, plants emerging from vegetative propagules, and established vegetation.

As used herein, immature vegetation refers to small vegetative plants prior to reproductive stage, and mature vegetation refers to vegetative plants during and after reproductive stage.

As used herein, agriculturally acceptable salts and esters refer to salts and esters that exhibit herbicidal activity or that are or can be converted in plants, water, or soil to the referenced herbicide or active moiety. Exemplary agriculturally acceptable esters are those that are or can be hydrolyzed, oxidized, metabolized, or otherwise converted, e.g., in plants, water, or soil, to the corresponding carboxylic acid which, depending upon the pH, may be in the dissociated or undissociated form.

Exemplary salts include those derived from alkali or alkaline earth metals and those derived from ammonia and amines. Exemplary cations include sodium, potassium, magnesium, and aminium cations of the formula:

$$R^1R^2R^3R^4N^+$$

wherein $R^1$, $R^2$, $R^3$ and $R^4$ each, independently represents hydrogen or $C_1$-$C_{12}$ alkyl, $C_3$-$C_{12}$ alkenyl, $C_3$-$C_{12}$ alkynyl, or aryl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

II. Synergistic Mixtures

Herbicidal compositions containing synergistically effective amounts of (a) fluroxypyr or an agriculturally acceptable ester or salt thereof and (b) an ALS-inhibiting herbicide. In some embodiments, the ALS-inhibiting herbicide is diclosulam, cloransulam, chlorimuron, or thifensulfuron, or an agriculturally acceptable ester or salt thereof.

A. Fluroxypyr

The compositions described herein contain fluroxypyr or an agriculturally acceptable salt or ester thereof. Fluroxypyr (2-[(4-amino-3,5-dichloro-6-fluoro-2-pyridinyl)oxy]-acetic acid) is a herbicide in the class of synthetic auxins. Fluroxypyr can be used, for example, for post-emergence foliar application to control broadleaf weeds, e.g., in small grain crops, to control *Rumex* spp. and *Urtica dioica* in pastures, and to control *Trifolium repens* in amenity grassland. Other exemplary uses include its use to control herbaceous and woody broadleaf weeds, e.g., in orchards and plantation crops, and broadleaf brush, e.g., in conifer forests. Its herbicidal activity is described in Tomlin, C. D. S., Ed. *The Pesticide Manual: A World Compendium*, 15th ed.; BCPC: Alton, 2009 (hereafter "*The Pesticide Manual*, Fifteenth Edition, 2009).

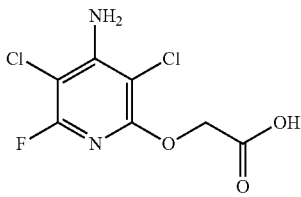 [SMILES: Nc1c(Cl)c(F)nc(OCC(=O)O)c1Cl]

Fluroxypyr can be used in its acid form (as shown above) or as an agriculturally acceptable salt or ester thereof. Exemplary agricuturally acceptable salts of fluroxypyr include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts. In certain embodiments, fluroxypyr is provided as an agriculturally acceptable ester. Suitable esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl and butoxyethyl esters, and aryl esters such as benzyl. Exemplary agriculturally acceptable esters of fluroxypyr butometyl and fluroxypyr MHE (fluroxypyr-methylheptyl ester, a.k.a, fluroxypyr-meptyl.

B. ALS-Inhibiting Herbicides

In addition to fluoroxypyr, the compositions include one or more acetolactate synthase (ALS)-inhibiting herbicides. ALS inhibitors disrupt the production of amino acids in the plant, which eventually leads to inhibition of DNA synthesis. ALS inhibitors include but are not limited to, sulfonylureas and triazolopyrimidine sulfonamides. In some embodiments, the composition can include an ALS inhibitor selected from sulfonylureas and triazolopyrimidine sulfonamides.

In some embodiments, the herbicidal composition comprises a herbicidally effective amount of: (a) fluroxypyr or an agriculturally acceptable ester or salt thereof and (b) a sulfonamide ALS-inhibiting herbicide. In some embodiments, the sulfonamide ALS-inhibiting herbicide is diclosulam or cloransulam, or an agriculturally acceptable ester or salt thereof.

In some embodiments, the herbicidal composition comprises a herbicidally effective amount of: (a) fluroxypyr or an agriculturally acceptable ester or salt thereof and (b) a sulfonylurea ALS-inhibiting herbicide. In some embodiment, the sulfonylurea ALS-inhibiting herbicide is chlorimuron or thifensulfuron, or an agriculturally acceptable ester or salt thereof.

1. Diclosulam

Diclosulam (N-(2,6-dichlorophenyl)-5-ethoxy-7-fluoro[1,2,4]triazolo[1,5-c]pyrimidine-2-sulfonamide), is a herbicide that inhibits ALS. Diclosulam can be used, for example, to control broadleaf weeds in peanuts and soybeans. Its herbicidal activity is described in *The Pesticide Manual*, Fifteenth Edition, 2009.

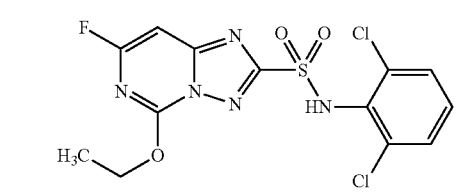 [SMILES: CCOc1nc(F)cc2nc(S(=O)(=O)Nc3c(Cl)cccc3Cl)nn12]

In certain embodiments of the compositions and methods described herein, fluroxypyr, or an agriculturally acceptable ester or salt thereof, is used in combination with diclosulam. With regard to the compositions, in some embodiments, the weight ratio of fluroxypyr or an agriculturally acceptable ester or salt thereof (acid equivalent) to diclosulam (active ingredient) is within the range of from about 1:2 to about 560:1. In certain embodiments, the weight ratio is about 25-200 of fluroxypyr, or an agriculturally acceptable ester or salt thereof, to about 1.1-25.2 of diclosulam. In certain embodiments, the weight ratio is within the range of from about 1:1 to about 182:1. In certain embodiments, the weight ratio is within the range of from about 1:1 to about 2:1, from about 2:1 to about 2.8:1, from about 2.8:1 to about 4:1, from about 4:1 to about 5.7:1, from about 5.7:1 to about 7.9:1, from about 7.9:1 to about 11.4:1, from about 11.4:1 to about 22.7:1, from about 22.7:1 to about 45.5:1, from about 45.5:1 to about 91:1, or from about 91:1 to about 182:1. In certain embodiments, the weight ratio is within the range from about 2:1 to about 92:1. In certain embodiments, the weight ratio is within the range from about 3:1 to about 46:1. In certain embodiments, the weight ratio is within the range from about 5:1 to about 23:1. In certain embodiments, the weight ratio is within the range from about 8:1 to about 23:1. In one embodiment, the weight ratio is within the range from about 5.7:1 to about 7.9:1. In another embodiment, the weight ratio is within the range from about 7.9:1 to about 11.4:1. In another embodiment, the weight ratio is within the range from about 11.4:1 to about 22.7:1. In one embodiment, the fluroxypyr, or an agriculturally acceptable ester or salt thereof, is fluroxypyr-meptyl.

With respect to the methods, in certain embodiments, the methods include contacting the undesirable vegetation with a composition described herein or components of a composition described herein, e.g., sequentially or simultaneously. In some embodiments, the composition is applied at an application rate from about 26 grams acid equivalent per hectare (g ae/ha) to about 610 g ae/ha based on the total amount of active ingredients in the composition. In certain embodiments, the composition is applied at an application rate from about 26 g ae/ha to about 226 g ae/ha based on the total amount of active ingredients in the composition. In certain embodiments, fluroxypyr, or an agriculturally acceptable ester or salt thereof, is applied at an application rate from about 25 g ae/ha to about 560 g ae/ha, and diclosulam is applied at an application rate from about 1 gram active ingredient per hectare (g ai/ha) to about 50 g ai/ha. In certain embodiments, fluroxypyr, or an agriculturally acceptable ester or salt thereof, is applied at an application rate from about 25 g ae/ha to about 200 g ae/ha, and diclosulam is applied at an application rate from about 1.1 g ai/ha to about 25.2 g ai/ha. In one embodiment, fluroxypyr, or an agriculturally acceptable ester or salt thereof, is applied at an application rate from about 25 g ae/ha to about 50 g ae/ha, and diclosulam is applied at an application rate from about 1.1 g ai/ha to about 8.8 g ai/ha. In another embodiment, fluroxypyr, or an agriculturally acceptable ester or salt thereof, is applied at an application rate from about 50 g ae/ha to about 100 g ae/ha, and diclosulam is applied at an application rate from about 2.2 g ai/ha to about 8.8 g ai/ha. In another embodiment, fluroxypyr, or an agriculturally acceptable ester or salt thereof, is applied at an application rate from about 100 g ae/ha to about 200 g ae/ha, and diclosulam is applied at an application rate from about 4.4 g ai/ha to about 25.2 g ai/ha. In one embodiment, the fluroxypyr, or an agriculturally acceptable ester or salt thereof, is fluroxypyr-meptyl.

In certain embodiments of the compositions and methods described herein, the only herbicidal active ingredients are fluroxypyr, or an agriculturally acceptable ester or salt thereof (e.g., fluroxypyr-meptyl) and diclosulam. In other embodiments, the compositions and methods described herein optionally utilize additional herbicidal active ingredients.

2. Cloransulam

Cloransulam (3-chloro-2-[[(5-ethoxy-7-fluoro[1,2,4]triazolo[1,5-c]pyrimidin-2-yl)sulfonyl]amino]benzoic acid) is a herbicide that inhibits ALS. Cloransulam can be used, for example, for post-emergence control of broadleaf weeds in soybeans and other broadleaf crops. Its herbicidal activity is described in *The Pesticide Manual*, Fifteenth Edition, 2009.

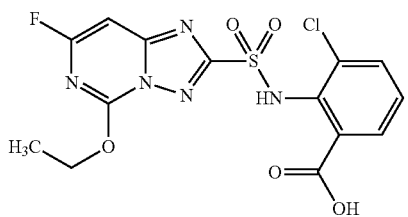 [SMILES: CCOc1nc(F)cc2nc(S(=O)(=O)Nc3c(Cl)cccc3C(=O)O)nn12]

Cloransulam can be provided in its acid form (as shown above) or as an agriculturally acceptable salt or ester thereof. Exemplary agriculturally acceptable salts of cloransulam include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts. In certain embodiments, cloransulam is provided as an agriculturally acceptable ester. Suitable esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl and butoxyethyl esters, and aryl esters such as benzyl. Exemplary agriculturally acceptable esters of cloransulam include, for example, cloransulam-methyl (methyl 3-chloro-2-[[(5-ethoxy-7-fluoro[1,2,4]triazolo[1,5-c]pyrimidin-2-yl)sulfonyl]amino]benzoate).

In certain embodiments of the compositions and methods described herein, fluroxypyr or an agriculturally acceptable ester or salt thereof is used in combination with cloransulam or an agriculturally acceptable ester or salt thereof. With regard to the compositions, in some embodiments, the weight ratio of fluroxypyr or an agriculturally acceptable ester or salt thereof (acid equivalent) to cloransulam or an agriculturally acceptable ester or salt thereof (active ingredient) is within the range from about 1:2 to about 560:1. In certain embodiments, the weight ratio is within the range of from about 1:1 to about 182:1. In certain embodiments, the weight ratio is within the range of from about 1:1 to about 2:1, from about 2:1 to about 2.8:1, from about 2.8:1 to about 4:1, from about 4:1 to about 5.7:1, from about 5.7:1 to about 7.9:1, from about 7.9:1 to about 11.4:1, from about 11.4:1 to about 22.7:1, from about 22.7:1 to about 45.5:1, from about 45.5:1 to about 91:1, or from about 91:1 to about 182:1. In certain embodiments, the weight ratio is about 25-100 of fluroxypyr or an agriculturally acceptable ester or salt thereof to about 1.1-8.8 of cloransulam or an agriculturally acceptable ester or salt thereof. In certain embodiments, the weight ratio is within the range from about 2.8:1 to about 91:1. In certain embodiments, the weight ratio is within the range from about 5.7:1 to about 91:1. In one embodiment, the weight ratio is within the range from about 5.7:1 to about 11.4:1. In another embodiment, the weight ratio is within the range from about 11.4:1 to about 23:1. In another embodiment, the weight ratio is within the range from about 23:1 to about 91:1. In one embodiment, the fluroxypyr or an agriculturally acceptable ester or salt thereof is fluroxypyr-meptyl. In one embodiment, the cloransulam or an agriculturally acceptable ester or salt thereof is cloransulam-methyl.

With respect to the methods, in certain embodiments, the methods comprise contacting the undesirable vegetation with a composition described herein or components of a composition described herein, e.g., sequentially or simultaneously. In some embodiments, the composition is applied at an application rate from about 26 g ae/ha to about 610 g ae/ha based on the total amount of active ingredients in the composition. In certain embodiments, the composition is applied at an application rate from about 26 g ae/ha to about 300 g ae/ha based on the total amount of active ingredients in the composition. In certain embodiments, the composition is applied at an application rate from about 26 g ae/ha to about 109 g ae/ha based on the total amount of active ingredients in the composition. In certain embodiments, fluroxypyr or an agriculturally acceptable ester or salt thereof is applied at an application rate from about 25 g ae/ha to about 560 g ae/ha, and cloransulam or an agriculturally acceptable ester or salt thereof is applied at an application rate from about 1 g ai/ha to about 50 g ai/ha. In certain embodiments, fluroxypyr or an agriculturally acceptable ester or salt thereof is applied at an application rate from about 25 g ae/ha to about 100 g ae/ha, and cloransulam or an agriculturally acceptable ester or salt thereof is applied at an application rate from about 1.1 g ai/ha to about 8.8 g ai/ha. In one embodiment, fluroxypyr or an agriculturally acceptable ester or salt thereof is applied at an application rate from about 25 g ae/ha to about 50 g ae/ha, and cloransulam or an agriculturally acceptable ester or salt thereof is applied at an application rate from about 1.1 g ai/ha to about 8.8 g ai/ha. In another embodiment, fluroxypyr or an agriculturally acceptable ester or salt thereof is applied at an application rate from about 50 g ae/ha to about 100 g ae/ha, and cloransulam or an agriculturally acceptable ester or salt thereof is applied at an application rate from about 1.1 g ai/ha to about 8.8 g ai/ha. In one embodiment, the fluroxypyr or an agriculturally acceptable ester or salt thereof is fluroxypyr-meptyl. In one embodiment, the cloransulam or an agriculturally acceptable ester or salt thereof is cloransulam-methyl.

In certain embodiments of the compositions and methods described herein, the only herbicidal active ingredients are fluroxypyr or an agriculturally acceptable ester or salt thereof (e.g., fluroxypyr-meptyl), and cloransulam or an agriculturally acceptable ester or salt thereof (e.g., cloransulam-methyl). In other embodiments, the compositions and methods described herein optionally utilize additional herbicidal active ingredients.

3. Chlorimuron

Chlorimuron ([[[[(4-chloro-6-methoxy-2-pyrimidinyl)amino]carbonyl]amino]-sulfonyl]benzoic acid) is a herbicide that inhibits ALS. Chlorimuron can be used, for example, for post-emergence control of important broadleaf weeds, such as cocklebur, pigweed, sunflower, annual morning glory and other broadleaf weeds in soybeans and peanuts. Its herbicidal activity is described in *The Pesticide Manual*, Fifteenth Edition, 2009.

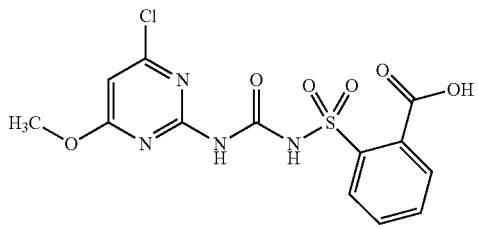 [SMILES: COc1cc(Cl)nc(NC(=O)NS(=O)(=O)c2ccccc2C(=O)O)n1]

Chlorimuron can be provided in its acid form (as shown above) or as an agriculturally acceptable salt or ester thereof. Exemplary agriculturally acceptable salts of chlorimuron include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts. In certain embodiments, chlorimuron is provided as an agriculturally acceptable ester. Suitable esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl and butoxyethyl esters, and aryl esters such as benzyl. Exemplary agriculturally acceptable esters of chlorimuron include, for example, chlorimuron-ethyl (ethyl 2-[[[[(4-chloro-6-methoxy-2-pyrimidinyl)amino]carbonyl]amino]-sulfonyl]benzoate).

In certain embodiments of the compositions and methods described herein, fluroxypyr or an agriculturally acceptable ester or salt thereof is used in combination with chlorimuron or an agriculturally acceptable ester or salt thereof. With regard to the compositions, in some embodiments, the weight ratio of fluroxypyr or an agriculturally acceptable ester or salt thereof (acid equivalent) to chlorimuron or an agriculturally acceptable ester or salt thereof (active ingredient) is within the range from about 1:3.6 to about 560:1. In certain embodiments, the weight ratio is within the range of from about 1:2 to about 560:1. In certain embodiments, the weight ratio is within the range of from about 1:1 to about 182:1. In certain embodiments, the weight ratio is within the range of from about 1:1 to about 2:1, from about 2:1 to about 2.8:1, from about 2.8:1 to about 4:1, from about 4:1 to about 5.7:1, from about 5.7:1 to about 7.9:1, from about 7.9:1 to about 11.4:1, from about 11.4:1 to about 22.7:1, from about 22.7:1 to about 45.5:1, from about 45.5:1 to about 91:1, or from about 91:1 to about 182:1. In certain embodiments, the weight ratio is about 25-100 of fluroxypyr or an agriculturally acceptable ester or salt thereof to about 1.1-8.8 of chlorimuron or an agriculturally acceptable ester or salt thereof. In certain embodiments, the weight ratio is within the range from about 2.8:1 to about 91:1. In certain embodiments, the weight ratio is within the range from about 2.8:1 to about 46:1. In one embodiment, the weight ratio is within the range from about 2.8:1 to about 45.5:1. In another embodiment, the weight ratio is within the range from about 11.4:1 to about 23:1. In one embodiment, the fluroxypyr or an agriculturally acceptable ester or salt thereof is fluroxypyr-meptyl. In one embodiment, the chlorimuron or an agriculturally acceptable ester or salt thereof is chlorimuron-ethyl.

With respect to the methods, in certain embodiments, the methods comprise contacting the undesirable vegetation with a composition described herein or components of a composition described herein, e.g., sequentially or simultaneously. In some embodiments, the composition is applied at an application rate from about 26 g ae/ha to about 650 g ae/ha based on the total amount of active ingredients in the composition. In certain embodiments, the composition is applied at an application rate from about 26 g ae/ha to about 109 g ae/ha based on the total amount of active ingredients in the composition. In certain embodiments, the composition is applied at an application rate from about 33 g ae/ha to about 103 g ae/ha based on the total amount of active ingredients in the composition. In certain embodiments, fluroxypyr or an agriculturally acceptable ester or salt thereof is applied at an application rate from about 25 g ae/ha to about 560 g ae/ha, and chlorimuron or an agriculturally acceptable ester or salt thereof is applied at an application rate from about 1 g ai/ha to about 90 g ai/ha. In certain embodiments, fluroxypyr or an agriculturally acceptable ester or salt thereof is applied at an application rate from about 25 g ae/ha to about 100 g ae/ha, and chlorimuron or an agriculturally acceptable ester or salt thereof is applied at an application rate from about 1.1 g ai/ha to about 8.8 g ai/ha. In one embodiment, fluroxypyr or an agriculturally acceptable ester or salt thereof is applied at an application rate from about 25 g ae/ha to about 50 g ae/ha, and chlorimuron or an agriculturally acceptable ester or salt thereof is applied at an application rate from about 1.1 g ai/ha to about 8.8 g ai/ha. In another embodiment, fluroxypyr or an agriculturally acceptable ester or salt thereof is applied at an application rate from about 50 g ae/ha to about 100 g ae/ha, and chlorimuron or an agriculturally acceptable ester or salt thereof is applied at an application rate from about 1.1 g ai/ha to about 2.2 g ai/ha. In one embodiment, the fluroxypyr or an agriculturally acceptable ester or salt thereof is fluroxypyr-meptyl. In one embodiment, the chlorimuron or an agriculturally acceptable ester or salt thereof is chlorimuron-ethyl.

In certain embodiments of the compositions and methods described herein, the only herbicidal active ingredients are fluroxypyr or an agriculturally acceptable ester or salt thereof (e.g., fluroxypyr-meptyl), and chlorimuron or an agriculturally acceptable ester or salt thereof (e.g., chlorimuron-ethyl). In other embodiments, the compositions and methods described herein optionally utilize additional herbicidal active ingredients.

4. Thifensulfuron

Thifensulfuron ([[[[(4-methoxy-6-methyl-1,3,5-triazin-2-yl)amino]carbonyl]amino]-sulfonyl]-2-thiophenecarboxylic acid) is a herbicide that inhibits ALS. Thifensulfuron can be used, for example, to control annual weeds in cereals, maize, soybeans and pasture. Its herbicidal activity is described in *The Pesticide Manual*, Fifteenth Edition, 2009.

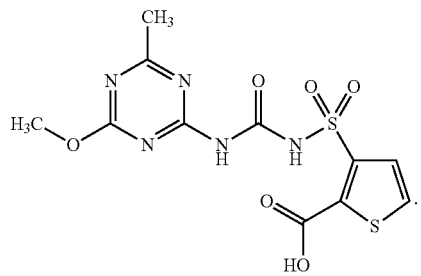 [SMILES: COc1nc(C)nc(NC(=O)NS(=O)(=O)c2ccsc2C(=O)O)n1]

Thifensulfuron can be provided in its acid form (as shown above) or as an agriculturally acceptable salt or ester thereof. Exemplary agricuturally acceptable salts of thifensulfuron include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts. In certain embodiments, thifensulfuron is provided as an agriculturally acceptable ester. Suitable esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl and butoxyethyl esters, and aryl esters such as benzyl. In certain embodiments, the corresponding carboxylic acid (thifensulfuron), carboxylate salt of thifensulfuron, other esters of thifensulfuron, e.g., alkyl or arylalkyl ester, or salt of thifensulfuron-methyl is utilized. Exemplary agriculturally acceptable esters of thifensulfuron include, for example, thifensulfuron-methyl (methyl 3-[[[[(4-methoxy-6-methyl-1,3,5-triazin-2-yl)amino]carbonyl]amino]sulfonyl]-2-thiophenecarboxylate).

In certain embodiments of the compositions and methods described herein, fluroxypyr or an agriculturally acceptable ester or salt thereof is used in combination with thifensulfuron or an agriculturally acceptable ester or salt thereof. With regard to the compositions, in some embodiments, the weight ratio of fluroxypyr or an agriculturally acceptable ester or salt thereof (acid equivalent) to thifensulfuron or an agriculturally acceptable ester or salt thereof (active ingredient) is within the range from about 1:1 to about 1120:1. In certain embodiments, the weight ratio is within the range from about 1.1:1 to about 500:1. In certain embodiments, the weight ratio is within the range from about 1.2:1 to about 334:1. In certain embodiments, the weight ratio is about 17.5-100 of fluroxypyr or an agriculturally acceptable ester or salt thereof to about 0.6-13 of thifensulfuron or an agriculturally acceptable ester or salt thereof. In certain embodiments, the weight ratio is within the range from about 1.3:1 to about 167:1. In certain embodiments, the weight ratio is within the range from about 1.3:1 to about 3.8:1, from about 3.8:1 to about 7.7:1, from about 7.7:1 to about 8:1, from about 8:1 to about 16:1, from about 16:1 to about 23:1, from about 23:1 to about 29:1, from about 29:1 to about 45.5:1, from about 45.5:1 to about 83:1, from about 83:1 to about 91:1, or from about 91:1 to about 167:1. In one embodiment, the weight ratio is within the range from about 1.3:1 to about 5:1. In another embodiment, the weight ratio is within the range from about 1.3:1 to about 10:1. In another embodiment, the weight ratio is within the range from about 1.3:1 to about 14:1. In another embodiment, the weight ratio is within the range from about 1.3:1 to about 18:1. In another embodiment, the weight ratio is within the range from about 1.3:1 to about 23:1. In another embodiment, the weight ratio is within the range from about 23:1 to about 91:1. In another embodiment, the weight ratio is within the range from about 35:1 to about 91:1. In another embodiment, the weight ratio is within the range from about 50:1 to about 91:1. In another embodiment, the weight ratio is within the range from about 60:1 to about 91:1. In another embodiment, the weight ratio is within the range from about 70:1 to about 91:1. In another embodiment, the weight ratio is within the range from about 91:1 to about 167:1. In another embodiment, the weight ratio is within the range from about 110:1 to about 167:1. In another embodiment, the weight ratio is within the range from about 130:1 to about 167:1. In another embodiment, the weight ratio is within the range from about 7.7:1 to about 29.2:1. In one embodiment, the fluroxypyr or an agriculturally acceptable ester or salt thereof is fluroxypyr-meptyl. In one embodiment, the thifensulfuron or an agriculturally acceptable ester or salt thereof is thifensulfuron-methyl.

With respect to the methods, in certain embodiments, the methods include contacting the undesirable vegetation with a composition described herein or components of a composition described herein, e.g., sequentially or simultaneously. In some embodiments, the composition is applied at an application rate from about 25.5 g ae/ha to about 585 g ae/ha based on the total amount of active ingredients in the composition. In certain embodiments, the composition is applied at an application rate from about 18 g ae/ha to about 113 g ae/ha based on the total amount of active ingredients in the composition. In certain embodiments, the composition is applied at an application rate from about 30.5 g ae/ha to about 102 g ae/ha based on the total amount of active ingredients in the composition. In certain embodiments, fluroxypyr or an agriculturally acceptable ester or salt thereof is applied at an application rate from about 25 g ae/ha to about 560 g ae/ha, and thifensulfuron or an agriculturally acceptable ester or salt thereof is applied at an application rate from about 0.5 g ai/ha to about 25 g ai/ha. In certain embodiments, fluroxypyr or an agriculturally acceptable ester or salt thereof is applied at an application rate from about 17.5 g ae/ha to about 100 g ae/ha, and thifensulfuron or an agriculturally acceptable ester or salt thereof is applied at an application rate from about 0.6 g ai/ha to about 13 g ai/ha. In one embodiment, fluroxypyr or an agriculturally acceptable ester or salt thereof is applied at an application rate from about 17.5 g ae/ha to about 50 g ae/ha, and thifensulfuron or an agriculturally acceptable ester or salt thereof is applied at an application rate from about 2.2 g ai/ha to about 13 g ai/ha. In another embodiment, fluroxypyr or an agriculturally acceptable ester or salt thereof is applied at an application rate from about 50 g ae/ha to about 100 g ae/ha, and thifensulfuron or an agriculturally acceptable ester or salt thereof is applied at an application rate from about 0.6 g ai/ha to about 2.2 g ai/ha. In one embodiment, the fluroxypyr or an agriculturally acceptable ester or salt thereof is fluroxypyr-meptyl. In one embodiment, the thifensulfuron or an agriculturally acceptable ester or salt thereof is thifensulfuron-methyl.

In certain embodiments of the compositions and methods described herein, the only herbicidal active ingredients are fluroxypyr or an agriculturally acceptable ester or salt thereof (e.g., fluroxypyr-meptyl) and thifensulfuron or an agriculturally acceptable ester or salt thereof (e.g., thifensulfuron-methyl). In other embodiments, the compositions and methods described herein optionally utilize additional herbicidal active ingredients. In one embodiment, the compositions do not contain and the methods do not utilize metsulfuron or an agriculturally acceptable ester or salt thereof. In one embodiment, the compositions do not contain and the methods do not utilize metsulfuron. In another embodiment, the compositions do not contain and the methods do not utilize metsulfuron-methyl. In another embodiment, the compositions contain and the methods utilize metsulfuron or an agriculturally acceptable ester or salt thereof, wherein the weight ratio of thifensulfuron, or an agriculturally acceptable ester or salt thereof to metsulfuron or an agriculturally acceptable ester or salt thereof is above or below 1:1.

In one embodiment, the composition comprising fluroxypyr or an agriculturally acceptable ester or salt thereof (e.g., fluroxypyr-meptyl) and thifensulfuron or an agriculturally acceptable ester or salt thereof (e.g., thifensulfuron-methyl) is not a suspension in oil. In another embodiment, the composition comprising fluroxypyr or an agriculturally acceptable ester or salt thereof (e.g., fluroxypyr-meptyl) and thifensulfuron or an agriculturally acceptable ester or salt thereof (e.g., thifensulfuron-methyl) is not a microcapsule.

In one embodiment, the herbicidal composition comprises a herbicidally effective amount of: (a) fluroxypyr or an agriculturally acceptable ester or salt thereof and (b) an ALS-inhibiting herbicide, wherein the ALS-inhibiting herbicide is diclosulam, cloransulam-methyl, chlorimuron-ethyl, or thifensulfuron-methyl.

In one embodiment of the compositions and methods provided herein, the fluroxypyr or an agriculturally acceptable ester or salt thereof is fluroxypyr-meptyl.

In one embodiment of the compositions and methods provided herein, the cloransulam or an agriculturally acceptable ester or salt thereof is cloransulam-methyl.

In one embodiment of the compositions and methods provided herein, the chlorimuron or an agriculturally acceptable ester or salt thereof is chlorimuron-ethyl.

In one embodiment of the compositions and methods provided herein, the thifensulfuron or an agriculturally acceptable ester or salt thereof is thifensulfuron-methyl.

In certain embodiments, the only herbicidal active ingredients utilized in the compositions and methods described herein are (a) the fluroxypyr or an agriculturally acceptable ester or salt thereof and (b) the ALS-inhibiting herbicide. Such compositions do not contain any herbicidally active or significantly herbicidally active ingredient other than the fluroxypyr or an agriculturally acceptable ester or salt thereof and the ALS-inhibiting herbicide, but may optionally contain additional components that are herbicidally inert. In some embodiments, the only herbicidally active ingredients are fluroxypyr or an agriculturally acceptable ester or salt thereof and diclosulam, cloransulam, chlorimuron, or thifensulfuron, or an agriculturally acceptable ester or salt thereof. In other embodiments, the compositions and methods described herein optionally utilize additional herbicidal active ingredients.

Furthermore, in some embodiments, the combination of fluroxypyr and ALS-inhibitors exhibit synergism, i.e., the herbicidal active ingredients are more effective in combination than when applied individually. Synergism has been defined as "an interaction of two or more factors such that the effect when combined is greater than the predicted effect based on the response of each factor applied separately." Shaner, D. L., Ed. *Herbicide Handbook*, 10$^{th}$ ed. Lawrence: Weed Science Society of America, 2014. In certain embodiments, the compositions exhibit synergy as determined by Colby's equation (Colby, S. R. Calculation of the synergistic and antagonistic response of herbicide combinations. *Weeds* 1967, 15, 20-22).

III. Herbicidal Formulations

In some embodiments, fluroxypyr and ALS inhibitors are used in combination with other herbicides which complement the spectrum of weeds controlled by these compounds at the application rate employed. In some embodiments, the compositions described herein and other complementary herbicides are applied at the same time, either as a combination formulation or as a tank mix, at the same time or as sequential applications.

The mixtures described herein can be applied in conjunction with one or more other herbicides to control a wider variety of undesirable vegetation. When used in conjunction with other herbicides, the composition can be formulated with the other herbicide or herbicides, tank-mixed with the other herbicide or herbicides or applied sequentially with the other herbicide or herbicides. Some of the herbicides that can be employed in conjunction with the compositions and methods described herein include, but are not limited to, optically active isomers, acid, salt, choline salt, and ester forms of the following herbicides: 4-CPA, 4-CPB, 4-CPP, 3,4-DA, 2,4-DB, 3,4-DB, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, bentazon, benthiocarb, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone (e.g., carfentrazone-ethyl), CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlornitrofen, chloropon, chlorotoluron, chloroxuron, chloroxynil, chlorpropham, chlorsulfuron, chlorthal, chlorthiamid, cinidon (e.g., cinidon-ethyl), cinmethylin, cinosulfuron, cisanilide, clethodim, cliodinate, clodinafop-propargyl, clofop, clomazone, clomeprop, cloprop, cloproxydim, clopyralid, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop (e.g., cyhalofop-butyl), cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethbenzamide, ethalfluralin, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P (e.g., fenoxaprop-P-ethyl), fenoxaprop-P-ethyl+isoxadifen-ethyl, fenoxasulfone, fenquinotrione, fenteracol, fenthiaprop, fentrazamide, fenuron, ferrous sulfate, flamprop, flamprop-M, flazasulfuron, florasulam, fluazifop, fluazifop-P (e.g., fluazifop-P-butyl), fluazolate, flucarbazone, flucetosulfuron, fluchloralin, flufenacet, flufenican, flufenpyr (e.g., flufenpyr-ethyl), flumetsulam, flumezin, flumiclorac (e.g., flumiclorac-pentyl), flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, flurtamone, fluthiacet, fomesafen, foramsulfuron, fosamine, fumiclorac, furyloxyfen, glufosinate-ammonium, glufosinate, halauxifen, halosafen, halosulfuron (e.g., halosulfuron-methyl), haloxydine, haloxyfopmethyl, haloxyfop-P (e.g., haloxyfop-P-methyl), hexachloroacetone, hexaflurate, hexazinone, imazamox, imazapic, imazapyr, imazaquin, imazethapyr, imazosulfuron, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham (e.g., phenmedipham-ethyl), phenobenzuron, phenylmercury acetate, picloram, picolinafen, pinoxaden, piperophos, potassium arsenite, potassium azide, potassium cyanate, pretilachlor, primisulfuron (e.g., primisulfuron-methyl), procyazine, prodiamine, profluazol, profluralin, profoxydim, proglinazine, prohexadione-calcium, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen (e.g., pyraflufen-ethyl), pyrasulfotole, pyrazogyl, pyrazolynate, pyrazosulfuron-ethyl, pyroxyfen, pyribenzoxim, pyributicarb, pyriclor, pyridafol, pyridate, pyriftalid, pyriminobac, pyrimisulfan, pyrithiobac-sodium, pyroxasulfone, pyroxsulam, quinclorac, quinmerac, quinoclamine, quinonamid, quizalofop, quizalofop-P (e.g., quizalofop-P-ethyl), rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thiobencarb, tiafenacil, tiocarbazil, tioclorim, tolpyralate, topramezone, tralkoxydim, triafamone, tri-allate, triasulfuron, triaziflam, tribenuron, tribenuron (e.g., tribenuron-methyl), tricamba, triclopyr (e.g., triclopyr choline salt), triclopyr, tridiphane, trietazine, trifloxysulfuron, trifludimoxazin, trifluralin, triflusulfuron, trifop, trifopsime, trihydroxytriazine, trimeturon, tripropindan, tritac, tritosulfuron, vernolate, xylachlor, benzyl 4-amino-3-chloro-5-fluoro-6-(4-chloro-2-fluoro-3-methoxyphenyl)pyridine-2-carboxylate, and mixtures thereof.

In some embodiments, the compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, microcapsules or wettable powders, or liquids, such as, for example, emulsifiable concentrates, solutions, emulsions or suspensions. They can also be provided as a pre-mix or tank-mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

In some embodiments, the compositions described herein are employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, R29148 and N-phenyl-sulfonylbenzoic acid amides, to enhance their selectivity. In some embodiments, the safeners are employed in rice, cereal, corn, or maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono-, di- and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in *McCutcheon's Detergents and Emulsifiers Annual*, MC Publishing Corporation: Ridgewood, N.J., 1998 and in *Encyclopedia of Surfactants, Vol. I-III*, Chemical Publishing Company: New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from about 0.0005 to 98 percent by weight. In some embodiments, the concentration is from about 0.0006 to 90 percent by weight. In compositions designed to be employed as concentrates, the active ingredients, in certain embodiments, are present in a concentration from about 0.1 to 98 weight percent, and in certain embodiments about 0.5 to 90 weight percent. Such compositions are, in certain embodiments, diluted with an inert carrier, such as water, before application. The diluted compositions usually applied to weeds or the locus of weeds contain, in certain embodiments, about 0.003 to 99 weight percent active ingredient and in certain embodiments contain about 0.08 to 25.0 weight percent.

IV. Methods of Application

Also provided herein are methods of controlling undesirable vegetation, comprising contacting the vegetation or the locus thereof, i.e., area adjacent to the vegetation, with a herbicidally effective amount of (a) fluroxypyr or an agriculturally acceptable ester or salt thereof and (b) an ALS-inhibiting herbicide including, but not limited to, diclosulam, cloransulam, chlorimuron, and thifensulfuron, or an agriculturally acceptable ester or salt thereof.

In one embodiment, provided herein are methods of controlling undesirable vegetation comprising contacting the vegetation or the locus thereof, i.e., area adjacent to the vegetation, with a herbicidally effective amount of (a) fluroxypyr or an agriculturally acceptable ester or salt thereof and (b) an ALS-inhibiting herbicide. In some embodiments, the ALS-inhibiting herbicide is diclosulam, cloransulam-methyl, chlorimuron-ethyl, or thifensulfuron-methyl.

Herbicidal activity is exhibited by the compounds when they are applied post-emergence directly to the plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, to relatively immature and mature undesirable vegetation to achieve the maximum control of weeds.

The compositions and methods provided herein can be utilized to control undesirable vegetation. Undesirable vegetation includes but is not limited to, undesirable vegetation that occurs in soybean, cotton, corn, canola/rapeseed, sugar beets, sunflower, alfalfa, sorghum, rice, wheat, barley, oats and other cereal crops, non-crop areas, including but not limited to pastures, grasslands, rangelands, fallowland, fencerows, parking areas, tank farms, storage areas, rights-of-way, utility areas, turf, forestry, aquatics, industrial vegetation management (IVM) and fallow-bed prior to planting crops; perennial crops where the application contacts the undesirable vegetation but does not contact the crop foliage, such as tree and vine orchards, including but not limited to citrus, grapes, almond, apple, apricot, avocado, beechnut, Brazil nut, butternut, cashew, cherry, chestnut, chinquapin, crab apple, date, feijoa, fig, filbert, hickory nut, kiwi, loquat, macadamia nut, mayhaws, nectarine, olives, peach, pear, pecan, persimmon, pistachio, plum, pomegranates, prune, quince and walnut; fruiting crops (e.g., blueberries, guava, papaya, strawberries, taro, blackberries and raspberries) and plantation crops (including but not limited to coffee, cacao, rubber and palm oil).

In some embodiments, the methods provided herein are utilized to control undesirable vegetation found in row crops. In certain embodiments, the undesirable vegetation is *Abutilon theophrasti* Medik. (velvetleaf, ABUTH), *Amaranthus palmeri* S. Wats. (Palmer amaranth, AMAPA), *Amaranthus* species (pigweeds and amaranths, AMASS), *Amaranthus retroflexus* (redroot pigweed, AMARE), *Amaranthus rudis* Sauer (common waterhemp, AMATA), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Cyperus esculentus* L. (yellow nutsedge, CYPES), *Cyperus rotundus* L. (purple nutsedge, CYPRO), *Datura stramonium* L. (jimsonweed, DATST), *Daucus carona* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida cordifolia* L. (heartleaf *sida*, SIDCO), *Sida spinosa* L. (prickly *sida*, SIDSP), *Sinapis arvensis* L. (wild mustard, SINAR), *Solanum ptychanthum* Dunal (eastern black nightshade, SOLPT) or *Xanthium strumarium* L. (common cocklebur, XANST).

In some embodiments, the methods provided herein are utilized to control undesirable vegetation found in tree and vine crops, perennial crops and non-crop areas. In certain embodiments, the undesirable vegetation is *Amaranthus palmeri* S. Wats. (Palmer amaranth, AMAPA), *Amaranthus* species (pigweeds and amaranths, AMASS), *Amaranthus retroflexus* (redroot pigweed, AMARE), *Amaranthus rudis* Sauer (common waterhemp, AMATA), *Sesbania exaltata* (Raf.) Cory/Rydb. Ex Hill (hemp *sesbania*, SEBEX), *Abutilon theophrasti* Medik. (velvetleaf, ABUTH), *Ambrosia artemisiifolia* L. (common ragweed, AMBEL), *Ambrosia psilostachya* DC. (western ragweed, AMBPS), *Ambrosia trifida* L. (giant ragweed, AMBTR), *Anoda cristata* (L.) Schlecht. (spurred *anoda*, ANVCR), *Asclepias syriaca* L. (common milkweed, ASCSY), *Bidens pilosa* L. (hairy beggarticks, BIDPI), *Borreria* species (BOISS), *Borreria alata* (Aubl.) DC. or *Spermacoce alata* Aubl. or *Spermacoce latifolia* (broadleaf buttonweed, BOILF), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Cyperus esculentus* L. (yellow nutsedge, CYPES), *Cyperus rotundus* L. (purple nutsedge, CYPRO), *Daucus carona* L. (wild carrot, DAUCA), *Euphorbia heterophylla* L. (wild poinsettia, EPHHL), *Euphorbia hirta* L. or *Chamaesyce hirta* (L.) Millsp. (garden spurge, EPHHI), *Euphorbia dentata* Michx. (toothed spurge, EPHDE), *Erigeron bonariensis* L. or *Conyza bonariensis* (L.) Cronq. (hairy fleabane, ERIBO), *Erigeron canadensis* L. or *Conyza canadensis* (L.) Cronq. (marestail, ERICA), *Conyza sumatrensis* (Retz.) E. H. Walker (tall fleabane, ERIFL), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Richardia* species (pusley, RCHSS), *Salsola tragus* L. (Russian thistle, SASKR), *Sida* species (*sida*, SIDSS), *Sida spinosa* L. (prickly *sida*, SIDSP), *Sinapis arvensis* L. (wild mustard, SINAR), *Solanum ptychanthum* Dunal (eastern black nightshade, SOLPT), *Tridax procumbens* L. (coat buttons, TRQPR) or *Xanthium strumarium* L. (common cocklebur, XANST).

In some embodiments, the methods provided herein are utilized to control undesirable vegetation in range and pasture area. In certain embodiments, the undesirable vegetation is *Amaranthus palmeri* S. Wats. (Palmer amaranth, AMAPA), *Amaranthus* species (pigweeds and amaranths, AMASS), *Ambrosia artemisiifolia* L. (common ragweed, AMBEL), *Ambrosia trifida* L. (giant ragweed, AMBTR), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Conyza canadensis* (L.) Cronq. (marestail, ERICA), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Salsola tragus* L. (Russian thistle, SASKR), *Sesbania exaltata* (Raf.) Cory/Rydb. Ex Hill (hemp *sesbania*, SEBEX), *Sida spinosa* L. (prickly *sida*, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE) or *Urtica dioica* L. (common nettle, URTDI).

In some embodiments, the methods provided herein are utilized to control undesirable vegetation in rice. In certain embodiments, the undesirable vegetation is *Cyperus difformis* L. (smallflower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SCPJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morningglory, IPOHE), *Lindernia dubia* (L.) Pennell (low false pimpernel, LIDDU), *Monochoria korsakowii* Regel & Maack (*monochoria*, MOOKA), *Monochoria vaginalis* (Burm. F.) C.

Presl ex Kuhth, (*monochoria*, MOOVA), *Murdannia nudiflora* (L.) Brenan (dovewed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp *sesbania*, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Cirsium arvense* (L.) Scop. (Canada thistle, CIRAR), *Galium aparine* L. (catchweed bedstraw, GALAP), *Kochia scoparia* (L.) Schrad. (*kochia*, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Mum (field violet, VIOAR) or *Viola tricolor* L. (wild violet, VIOTR).

In some embodiments, the combination of fluroxypyr and ALS inhibitors is used to synergistically control *Abutilon theophrasti* (velvetleaf, ABUTH), *Amaranthus retroflexus* L. (redroot pigweed, AMARE), *Amaranthus rudis* Sauer (common waterhemp, AMATA), *Amaranthus palmeri* S. Wats. (Palmer amaranth, AMAPA), *Chenopodium album* (common lambsquarter, CHEAL), *Commelina benghalensis* (tropical spiderwort, COMBE), *Polygonum convolvulus* L. (wild buckwheat, POLCO) and *Sida cordifolia* L. (heartleaf *sida*, SIDCO).

In certain embodiments, the methods and compositions utilizing fluroxypyr or an agriculturally acceptable ester or salt thereof (e.g., fluroxypyr-meptyl) and diclosulam are used to control ABUTH, AMATA, CHEAL, COMBE, or SIDCO.

In certain embodiments, the methods and compositions utilizing fluroxypyr or an agriculturally acceptable ester or salt thereof (e.g., fluroxypyr-meptyl) and cloransulam or an agriculturally acceptable ester or salt thereof (e.g., cloransulam-methyl) are used to control ABUTH, AMATA, or CHEAL.

In certain embodiments, the methods and compositions utilizing fluroxypyr or an agriculturally acceptable ester or salt thereof (e.g., fluroxypyr-meptyl) and chlorimuron or an agriculturally acceptable ester or salt thereof (e.g., chlorimuron-ethyl), are used to control ABUTH or AMATA.

In certain embodiments, the methods and compositions utilizing fluroxypyr or an agriculturally acceptable ester or salt thereof (e.g., fluroxypyr-meptyl) and thifensulfuron or an agriculturally acceptable ester or salt thereof (e.g., thifensulfuron-methyl) are used to control AMARE, ABUTH, AMAPA, CHEAL, or POLCO.

Fluroxypyr and ALS inhibitors may be used to control herbicide resistant or tolerant weeds. The methods employing the combination of fluroxypyr and ALS inhibitors and the compositions described herein may also be employed to control herbicide resistant or tolerant weeds. Exemplary resistant or tolerant weeds include but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, dimethoxy-pyrimidines, triazolopyrimidine sulfonamides, sulfonylamino-carbonyl-triazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxy-propionates, cyclohexanediones, phenylpyrazolines), synthetic auxins (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenyl-phthalimides, oxadiazoles, oxazolidinediones, phenylpyrazoles, pyrimidinediones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to single or multiple herbicides, biotypes with resistance or tolerance to single or multiple chemical classes, biotypes with resistance or tolerance to single or multiple herbicide modes-of-action, and biotypes with single or multiple resistance or tolerance mechanisms (e.g., target site resistance or metabolic resistance).

The compositions and methods described herein can also be used to control undesirable vegetation in glyphosate-, 2,4-D- and glufosinate-tolerant soybeans, corn, or cotton which may also be combined with traits providing dicamba-tolerance (e.g., DMO), pyridyloxy auxin-tolerance (e.g., aad-12, aad-13), auxin-tolerance, auxin transport inhibitor-tolerance, acetyl CoA carboxylase (ACCase) inhibitor-herbicide tolerance [e.g., aryloxyphenoxypropionate, cyclohexanedione, and phenylpyrazoline chemistries (e.g., various ACCase genes and aad-1 gene)], acetolactate synthase (ALS)-inhibiting herbicide tolerance (e.g., imidazolinone, sulfonylurea, triazolopyrimidine sulfonamide, pyrmidinylthiobenzoate, and other chemistries=AHAS, Csr1, SurA), 4-hydroxyphenyl-pyruvate dioxygenase (HPPD) inhibitor-tolerance, phytoene desaturase (PDS) inhibitor-tolerance (e.g., pds, CYP1A1, CYP2B6, CYP2C19), carotenoid biosynthesis inhibitor-tolerance, protoporphyrinogen oxidase (PPO) inhibitor-tolerance, cellulose biosynthesis inhibitor-tolerance (e.g., ixr2-1, CYP1A1), mitosis inhibitor-tolerance, microtubule inhibitor-tolerance, very long chain fatty acid (VLCFA) inhibitor-tolerance (e.g., CYP1A1, CYP2B6, CYP2C19), fatty acid and lipid biosynthesis inhibitor-tolerance (e.g., CYP1A1), photosystem I inhibitor-tolerance (e.g., SOD), photosystem II inhibitor (triazine, nitrile, and phenylurea chemistries) tolerance (e.g., psbA, CYP1A1, CYP2B6, CYP2C19, and Bxn), in crops (such as, but not limited to, soybean, corn, cotton, canola/oilseed rape, rice, cereals, sorghum, sunflower, sugar beet, sugarcane, alfalfa and turf), for example, in conjunction with glyphosate, 5-enolpyruvylshikimate-3-phosphate (EPSP) synthase inhibitors, glutamine synthase inhibitors, dicamba, phenoxy auxins, pyridyloxy auxins, synthetic auxins, auxin transport inhibitors, aryloxyphenoxypropionates, cyclohexanediones, phenylpyrazolines, ACCase inhibitors, imidazolinones, sulfonylureas, pyrimidinylthiobenzoates, dimethoxy-pyrimidines, triazolopyrimidine sulfonamides, sulfonylaminocarbonyltriazolinones, ALS or acetohydroxy acid synthase (AHAS) inhibitors, HPPD inhibitors, PDS inhibitors, carotenoid biosynthesis inhibitors, PPO inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil. The compositions and methods may be used in controlling undesirable vegetation in soybeans, corn, or cotton possessing single and multiple or stacked traits conferring tolerance to single or multiple chemistries and/or inhibitors of multiple modes-of-action. In some embodiments, glyphosate-dimethylammonium (glyphosate-DMA), 2,4-D-choline, and glufosinate-ammonium are used in combination with herbicides that are selective for the soybeans, corn or cotton being treated and which complement the spectrum of weeds controlled by these compounds at the application rate employed. In some embodiments, the compositions described herein and other complementary herbicides are applied at the same time, either as a combination formulation or as a tank mix, at the same time or as sequential applications.

As used herein, 2,4-D-tolerance refers to soybeans, corn, cotton, wheat, barley, oats, sorghum, sunflower, sugarcane, sugar beet, canola/rapeseed and rice that are genetically modified to be tolerant to 2,4-D. Examples of 2,4-D-tolerance includes soybeans containing the aad-12 gene which confers tolerance to 2,4-D (U.S. Pat. No. 8,283,522 B2). As used herein, 2,4-D-tolerant corn refers to corn that is genetically modified to be tolerant to 2,4-D. Examples of 2,4-D-tolerant corn include corn containing the aad-1 gene which confers tolerance to 2,4-D (U.S. Pat. No. 7,838,733 B2). As used herein, 2,4-D-tolerant cotton refers to cotton that is genetically modified to be tolerant to 2,4-D. Examples of 2,4-D-tolerant cotton include cotton containing the aad-12 gene which confers tolerance to 2,4-D. However, tolerance in each of these crops by the aad-1 or aad-12 genes or with alternative genes providing additional or alternative tolerance to transgenic crops [e.g., aad-13 (U.S. Pat. No. 8,278,505 B2), tfdA (U.S. Pat. No. 6,153,401 A), or 24dt02 (CN103060279)] are considered to be included within the scope of the 2,4-D- and glufosinate-tolerant soybeans, corn, or cotton described herein.

As used herein, glyphosate tolerance refers to soybeans, corn, cotton, wheat, barley, oats, sorghum, sugar beets, sunflower, canola/oilseed rape and rice that are genetically modified to be tolerant to glyphosate. Glyphosate tolerance can be provided, for example, by the CP4 gene (U.S. Pat. No. 5,627,061 A) or 2mEPSPS (U.S. Pat. No. 6,566,587 B1) as shown herein; however, glyphosate tolerance could also be conferred within the scope of glyphosate-, 2,4-D-, and glufosinate-tolerant-soybeans, corn, cotton, wheat, barley, oats, sorghum, sunflower, sugarcane, sugar beet, canola/rapeseed and rice described herein by other genes providing transgenic crop tolerance to glyphosate [e.g., AroA and other Class II EPSPS (U.S. Pat. No. 7,893,234 B2); GLG23 and other Class III EPSPS (U.S. Pat. No. 7,700,842 B2); GAT (U.S. Pat. No. 7,405,074 B2), Gox (U.S. Pat. No. 5,463,175 A), or other glyphosate-metabolism gene; or DGT-28 or other Class IV EPSPS (U.S. Patent Application Publication 20130217577A1)] are considered to be included within the scope of the 2,4-D-, glyphosate- and glufosinate-tolerant soybeans, corn, cotton, wheat, barley, oats, sorghum and rice described herein.

As used herein, glufosinate tolerance refers to soybeans, corn, cotton, wheat, barley, oats, sunflower, alfalfa, canola/oilseed rape, sugar beet, and rice that are genetically modified to be tolerant to glufosinate. Glufosinate tolerance can be provided, for example, by the pat gene (U.S. Pat. No. 5,587,903 A) as shown herein; however, glufosinate tolerance could also be conferred within the scope of the 2,4-D- and glufosinate-tolerant soybeans, corn, or cotton described herein by other genes providing transgenic crop tolerance to glufosinate [e.g., bar (U.S. Pat. No. 5,561,236 A) and dsm2 (PCT International Application WO2008070845)].

The components of the mixtures described herein can be applied either separately, sequentially, tank-mixed or as part of a mixture or multipart herbicidal system.

The present compositions can be applied to weeds or their locus by the use of conventional ground or aerial dusters, sprayers, and granule applicators, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Example 1: Evaluation of Herbicidal Activity of Mixtures Under Greenhouse Conditions Methodology Seeds of the desired test plant species were planted in a peat-based potting soil, Metro-Mix 360® in plastic pots with a surface area of 128 square centimeters ($cm^2$). Metro-Mix 360® consists of formulated Canadian sphagnum peat moss, coarse perlite, bark ash, a starter nutrient charge (with gypsum), a slow-release nitrogen and dolomitic limestone. The plants were grown for 7-19 days in a greenhouse with an approximate 14-hour (h) photoperiod which was maintained at about 29° C. during the day and 26° C. during the night. Nutrients and water were added on a regular basis and supplemental lighting was provided with overhead metal halide 1000-Watt lamps as necessary. The plants were treated with postemergence foliar applications when they reached the third to fourth true leaf stage. All treatments were applied using a randomized complete block trial design, with 4 replications per treatment.

Treatments consisted of the compounds as listed in Tables 1 to 4, each compound applied alone and in combination. Commercially formulated products of fluroxypyr-meptyl (STARANE™, 333 grams acid equivalent per liter (g ae/L) EC), diclosulam (SPIDER® 84WG), cloransulam-methyl (FIRSTRATE™ 84WG), chlorimuron-ethyl (CLASSIC® 25WG) and thifensulfuron-methyl (HARMONY® 50SG). Formulated amounts of fluroxypyr-meptyl, diclosulam, cloransulam-methyl, chlorimuron-ethyl and thifensulfuron-methyl were placed in 60 milliliter (mL) glass vials and dissolved in a volume of 30 or 60 mL of a water solution containing Agri-dex crop oil concentrate in a 1% volume per volume (v/v) ratio. Compound requirements are based upon either a 30- or a 60-mL application volume at a rate of 200 liters per hectare (L/ha). Spray solutions of the mixtures were prepared by adding the stock solutions to the appropriate amount of dilution solution to form either a 30- or a 60-mL spray solution with active ingredients in single and two-way combinations. Formulated compounds were applied to the plant material with an overhead Generation III Research Sprayer manufactured by DeVries Manufacturing in Hollandale, Minn., USA. The track sprayer was equipped with an 8003E nozzle calibrated to deliver 200 L/ha at a spray height of 18 inches (43 centimeters (cm)) above average plant canopy.

The treated plants and untreated control plants were placed in a greenhouse as described above and watered by sub-irrigation to prevent wash-off of the test compounds.

Evaluation

Treatments were rated at 7 to 21 days after application (DAA) as compared to the untreated control plants. Visual weed control was scored on a scale of 0 to 100 percent where 0 corresponds to no injury and 100 corresponds to complete kill.

Example 2: Evaluation of Herbicidal Activity of Mixtures Under Field Conditions

Methodology

Field trials were conducted using standard herbicide small plot research methodology. Plots varied from 3×3.3 meter (m) to 4.5×10 m (width×length) with 4 replicates per treatment. The crops used in the field trials were grown using normal cultural practices for land preparation, fertilization, seeding and maintenance to ensure good growth of the crop and the weeds.

All treatments in the field trials were applied using either pressurized air or carbon dioxide ($CO_2$) backpack or bicycle sprayers calibrated to apply 100-187 L/ha spray volume. Flat Fan spray nozzles were used in all trials, with water as the diluent applied at 275-300 kilopascals (kPa). Weed sizes at application ranged from 10 to 40 cm tall. Commercially available products of fluroxypyr-meptyl (STARANE™, 180 and 333 g ae/L EC), diclosulam (SPIDER® 84WG), and thifensulfuron-methyl (HARMONY® 75WG) were mixed in water at appropriately formulated product rates to achieve the desired rates based on a unit area of application (hectare) to achieve the desired rates as shown. No adjuvants were tank-mixed with any treatments applied in the field trials. Treatments were rated at 14-26 days after application as compared to the untreated control plants. Visual weed control was scored on a scale of 0 to 100 percent where 0 corresponds to no injury and 100 corresponds to complete kill.

Evaluation

The treated plots and control plots were rated blind at various intervals after application. Ratings were reported on a Percent (%) Visual Control basis, where 0 corresponds to no visual effect/weed control and 100 corresponds to complete kill of the target weeds.

Tables 1-4 demonstrate the herbicidal synergistic efficacy of fluroxypyr-meptyl tank mixes on weed control. All treatment results, both for the single product and mixtures, are an average of 4 replicates and the tank-mix interactions are significant at the P>0.05 level.

The weed spectrum included, but was not limited to, *Abutilon theophrasti* (velvetleaf, ABUTH), *Amaranthus retroflexus* L. (redroot pigweed, AMARE), *Amaranthus rudis* Sauer (common waterhemp, AMATA), *Amaranthus palmeri* S. Wats. (Palmer amaranth, AMAPA), *Chenopodium album* (common lambsquarters, CHEAL), *Commelina benghalensis* (tropical spiderwort, COMBE), *Polygonum convolvulus* L. (wild buckwheat, POLCO) and *Sida cordifolia* L. (heartleaf *sida*, SIDCO).

Colby's equation was used to determine the herbicidal effects expected from the mixtures (Colby, S. R. Calculation of the synergistic and antagonistic response of herbicide combinations. *Weeds* 196715, 20-22). A t-test (alpha=0.05) between Colby predictions and observed combinations was used to test for significant differences indicating synergy or antagonism. The results presented in the Tables were significant according to the described criteria.

The following equation was used to calculate the expected activity of mixtures containing two active ingredients, A and B:

$$\text{Expected} = A + B - (A \times B/100)$$

A=observed efficacy of active ingredient A at the same concentration as used in the mixture;
B=observed efficacy of active ingredient B at the same concentration as used in the mixture.

The results are summarized in Tables 1-4.

TABLE 1

Synergistic Postemergence Herbicidal Weed Control (Percent (%) Visual Control) from Combinations of Fluroxypyr-meptyl and Diclosulam in Greenhouse Trials at 8 to 26 Days After Application 1 (DAA1).

| | | Fluroxypyr-meptyl | | Diclosulam | | Combination | Colby |
|---|---|---|---|---|---|---|---|
| Weed Bayer | Evaluation Interval | g ae/ha | Mean % weed control | g ai/ha | Mean % weed control | Measured mean % weed control | predicted mean % weed control |
| ABUTH | 14DAA1 | 25 | 70.0 | 1.1 | 28.8 | 98.5 | 78.3 |
| ABUTH | 21DAA1 | 25 | 72.5 | 1.1 | 30.0 | 100.0 | 80.6 |
| AMATA | 21DAA1 | 50 | 37.5 | 8.8 | 28.8 | 96.3 | 55.5 |
| AMATA | 8DAA1 | 50 | 60.0 | 8.8 | 51.3 | 95.5 | 80.4 |
| CHEAL | 8DAA1 | 50 | 43.3 | 8.8 | 38.3 | 75.0 | 66.2 |
| CHEAL | 14DAA1 | 50 | 20.0 | 2.2 | 3.3 | 43.3 | 22.3 |
| CHEAL | 14DAA1 | 50 | 20.0 | 8.8 | 21.7 | 73.3 | 37.3 |
| AMATA | 14DAA1 | 50 | 43.8 | 8.8 | 27.5 | 95.0 | 59.9 |
| CHEAL | 21DAA1 | 50 | 18.3 | 2.2 | 5.0 | 43.3 | 22.3 |
| CHEAL | 21DAA1 | 50 | 18.3 | 4.4 | 16.7 | 41.7 | 32.8 |
| CHEAL | 21DAA1 | 50 | 18.3 | 8.8 | 31.7 | 70.0 | 43.6 |
| AMATA | 14DAA1 | 100 | 37.5 | 4.4 | 28.8 | 63.8 | 54.8 |

TABLE 1-continued

Synergistic Postemergence Herbicidal Weed Control (Percent (%) Visual Control) from Combinations of Fluroxypyr-meptyl and Diclosulam in Greenhouse Trials at 8 to 26 Days After Application 1 (DAA1).

| Weed Bayer | Evaluation Interval | Fluroxypyr-meptyl | | Diclosulam | | Combination | Colby |
|---|---|---|---|---|---|---|---|
| | | g ae/ha | Mean % weed control | g ai/ha | Mean % weed control | Measured mean % weed control | predicted mean % weed control |
| AMATA | 14DAA1 | 100 | 37.5 | 8.8 | 27.5 | 65.0 | 55.8 |
| CHEAL | 21DAA1 | 100 | 21.0 | 4.4 | 16.7 | 48.3 | 34.0 |
| AMATA | 21DAA1 | 100 | 38.8 | 4.4 | 25.0 | 65.0 | 52.9 |
| AMATA | 21DAA1 | 100 | 38.8 | 8.8 | 28.8 | 66.3 | 56.7 |
| COMBE | 14DAA1 | 200 | 27.5 | 25.2 | 41.3 | 72.5 | 57.5 |
| COMBE | 26DAA1 | 200 | 25.0 | 25.2 | 17.5 | 61.3 | 37.8 |
| SIDCO | 14DAA1 | 200 | 30.0 | 25.2 | 23.3 | 61.7 | 49.0 |

TABLE 2

Synergistic Postemergence Herbicidal Weed Control (% Visual Control) from Combinations of Fluroxypyr-meptyl and Cloransulam-methyl in Field Trials at 8 to 21 Days After Application 1 (DAA1).

| Weed Bayer | Evaluation Interval | Fluroxypyr-meptyl | | Cloransulam-methyl | | Combination | Colby |
|---|---|---|---|---|---|---|---|
| | | g ae/ha | Mean % weed control | g ai/ha | Mean % weed control | Measured mean % weed control | predicted mean % weed control |
| AMATA | 8DAA1 | 25 | 42.5 | 4.4 | 58.8 | 98.8 | 76.3 |
| CHEAL | 8DAA1 | 25 | 33.3 | 4.4 | 35.0 | 68.3 | 56.7 |
| ABUTH | 14DAA1 | 25 | 68.3 | 1.1 | 38.3 | 92.0 | 80.5 |
| ABUTH | 14DAA1 | 25 | 70.0 | 4.4 | 70.0 | 99.0 | 91.2 |
| CHEAL | 14DAA1 | 25 | 10.0 | 4.4 | 11.7 | 71.7 | 20.5 |
| AMATA | 14DAA1 | 25 | 21.3 | 4.4 | 38.8 | 97.5 | 51.9 |
| ABUTH | 21DAA1 | 25 | 71.7 | 1.1 | 40.0 | 94.0 | 82.8 |
| ABUTH | 21DAA1 | 25 | 72.5 | 4.4 | 70.0 | 100.0 | 91.8 |
| CHEAL | 21DAA1 | 25 | 18.3 | 4.4 | 11.0 | 73.3 | 27.3 |
| AMATA | 21DAA1 | 25 | 22.5 | 4.4 | 37.5 | 95.0 | 52.0 |
| CHEAL | 21DAA1 | 50 | 18.3 | 8.8 | 10.0 | 36.7 | 27.2 |
| CHEAL | 14DAA1 | 100 | 33.3 | 1.1 | 16.7 | 55.0 | 44.7 |
| CHEAL | 21DAA1 | 100 | 21.0 | 1.1 | 8.3 | 43.3 | 28.8 |
| CHEAL | 21DAA1 | 100 | 21.0 | 4.4 | 11.0 | 43.3 | 30.0 |
| CHEAL | 21DAA1 | 100 | 21.0 | 8.8 | 10.0 | 53.3 | 28.7 |

TABLE 3

Synergistic Postemergence Herbicidal Weed Control (% Visual Control) from Combinations of Fluroxypyr-meptyl and Chlorimuron-ethyl in Field Trials at 7 to14 Days After Application 1 (DAA1).

| Weed Bayer | Evaluation Interval | Fluroxypyr-meptyl | | Chlorimuron-ethyl | | Combination | Colby |
|---|---|---|---|---|---|---|---|
| | | g ae/ha | Mean % weed control | g ai/ha | Mean % weed control | Measured mean % weed control | predicted mean % weed control |
| AMATA | 7DAA1 | 25 | 25.0 | 8.8 | 41.3 | 68.8 | 55.8 |
| AMATA | 14DAA1 | 25 | 7.5 | 8.8 | 28.8 | 46.3 | 34.1 |
| ABUTH | 14DAA1 | 50 | 67.0 | 1.1 | 56.3 | 89.3 | 85.1 |
| ABUTH | 14DAA1 | 100 | 80.8 | 2.2 | 62.5 | 95.0 | 92.5 |

TABLE 4

Synergistic Postemergence Herbicidal Weed Control (% Visual Control) from Combinations of Fluroxypyr-meptyl and Thifensulfuron-methyl in Field Trials at 7 to 21 Days After Application 1 (DAA1).

| Weed Bayer | Evaluation Interval | Fluroxypyr-meptyl | | Thifensulfuron-methyl | | Combination | Colby |
|---|---|---|---|---|---|---|---|
| | | g ae/ha | Mean % weed control | g ai/ha | Mean % weed control | Measured mean % weed control | predicted mean % weed control |
| AMARE | 21DAA1 | 17.5 | 3.8 | 13.0 | 90.0 | 97.5 | 90.4 |
| CHEAL | 21DAA1 | 17.5 | 3.8 | 13.0 | 90.0 | 97.5 | 90.4 |
| POLCO | 21DAA1 | 17.5 | 2.5 | 13.0 | 90.0 | 97.5 | 90.5 |
| AMAPA | 7DAA1 | 50 | 48.8 | 2.2 | 22.5 | 75.0 | 60.4 |
| ABUTH | 14DAA1 | 100 | 80.8 | 0.6 | 56.3 | 100.0 | 91.3 |
| ABUTH | 14DAA1 | 100 | 80.8 | 1.1 | 73.8 | 99.0 | 94.8 |

AMARE = *Amaranthus retroflexus* L. (redroot pigweed)
ABUTH = *Abutilon theophrasti* (velvetleaf)
AMATA = *Amaranthus rudis* Sauer (common waterhemp)
AMAPA = *Amaranthus palmeri* S. Wats. (Palmer amaranth)
CHEAL = *Chenopodium album* (common lambsquarters)
COMBE = *Commelina benghalensis* (tropical spiderwort)
SIDCO = *Sida cordifolia* L. (heartleaf sida)
POLCO = *Polygonum convolvulus* L. (wild buckwheat)
g ae/ha = grams acid equivalent per hectare
g ai/ha = grams active ingredient per hectare
DAA1 = Days After Application 1

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative composition materials and method steps disclosed herein are specifically described, other combinations of the composition materials and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

What is claimed is:

1. A herbicidal composition comprising a herbicidally effective amount of (a) fluroxypyr or an agriculturally acceptable ester or salt thereof and (b) an ALS-inhibiting herbicide, wherein the ALS-inhibiting herbicide is selected from the group consisting of diclosulam, cloransulam, chlorimuron, and thifensulfuron, and an agriculturally acceptable ester or salt thereof, wherein when (b) is diclosulam or an agriculturally acceptable ester or salt thereof, the weight ratio of (a) and (b) is from about 2.8:1 to about 45.5:1, when (b) is cloransulam or an agriculturally acceptable ester or salt thereof, the weight ratio of (a) and (b) is from about 2.8:1 to about 182:1, when (b) is chlorimuron or an agriculturally acceptable ester or salt thereof, the weight ratio of (a) and (b) is from about 2.8:1 to about 91:1, and when (b) is thifensulfuron or an agriculturally acceptable ester or salt thereof, the weight ratio of (a) and (b) is from about 1:1 to about 334:1.

2. The composition of claim 1, wherein the fluroxypyr or an agriculturally acceptable ester or salt thereof is fluroxypyr-meptyl.

3. The composition of claim 1, wherein the ALS inhibiting herbicide is diclosulam.

4. The composition of claim 3, wherein the weight ratio of fluroxypyr or an agriculturally acceptable ester or salt thereof to diclosulam is within the range of from about 5:1 to about 23:1.

5. The composition of claim 1, wherein the ALS-inhibiting herbicide is cloransulam or an agriculturally acceptable ester or salt thereof.

6. The composition of claim 5, wherein the weight ratio of fluroxypyr or an agriculturally acceptable ester or salt thereof to cloransulam or an agriculturally acceptable ester or salt thereof is within the range of from about 2.8:1 to about 91:1.

7. The composition of claim 6, wherein the weight ratio of fluroxypyr or an agriculturally acceptable ester or salt thereof to cloransulam or an agriculturally acceptable ester or salt thereof is within the range of from about 5.7:1 to about 91:1.

8. The composition of claim 5, wherein the cloransulam or an agriculturally acceptable ester or salt thereof, is cloransulam-methyl.

9. The composition of claim 1, wherein the ALS-inhibiting herbicide is chlorimuron or an agriculturally acceptable ester or salt thereof.

10. The composition of claim 9, wherein the weight ratio of fluroxypyr or an agriculturally acceptable ester or salt thereof to chlorimuron or an agriculturally acceptable ester or salt thereof is within the range of from about 2.8:1 to about 45.5:1.

11. The composition of claim 9, wherein the chlorimuron or an agriculturally acceptable ester or salt thereof is chlorimuron-ethyl.

12. The composition of claim 1, wherein the ALS-inhibiting herbicide is thifensulfuron or an agriculturally acceptable ester or salt thereof.

13. The composition of claim 12, wherein the weight ratio of fluroxypyr or an agriculturally acceptable ester or salt thereof to thifensulfuron or an agriculturally acceptable ester or salt thereof is within the range of from about 1.3:1 to about 167:1.

14. The composition of claim 13, wherein the weight ratio of fluroxypyr or an agriculturally acceptable ester or salt thereof to thifensulfuron or an agriculturally acceptable ester or salt thereof is within the range of from about 91:1 to about 167:1.

15. The composition of claim 12, wherein the thifensulfuron or an agriculturally acceptable ester or salt thereof is thifensulfuron-methyl.

16. The composition of claim 1, wherein fluroxypyr or an agriculturally acceptable ester or salt thereof and the ALS-inhibiting herbicide are the only herbicidal active ingredients.

17. The composition of claim 1, further comprising a herbicidally effective amount of an additional herbicide.

18. The composition of claim 1, further comprising an agriculturally acceptable adjuvant.

19. A method of controlling undesirable vegetation comprising contacting the undesirable vegetation or the locus thereof with a herbicidally effective amount of (a) fluroxypyr or an agriculturally acceptable ester or salt thereof and (b) an ALS-inhibiting herbicide, wherein the ALS-inhibiting herbicide is selected from the group consisting of diclosulam, cloransulam, chlorimuron, or thifensulfuron, or an agriculturally acceptable ester or salt thereof,
wherein when (b) is diclosulam or an agriculturally acceptable ester or salt thereof, the weight ratio of (a) and (b) is from about 2.8:1 to about 45.5:1,
when (b) is cloransulam or an agriculturally acceptable ester or salt thereof, the weight ratio of (a) and (b) is from about 2.8:1 to about 182:1,
when (b) is chlorimuron or an agriculturally acceptable ester or salt thereof, the weight ratio of (a) and (b) is from about 2.8:1 to about 91:1, and
when (b) is thifensulfuron or an agriculturally acceptable ester or salt thereof, the weight ratio of (a) and (b) is from about 1:1 to about 334:1.

20. The method of claim 19, wherein the fluroxypyr or an agriculturally acceptable ester or salt thereof is fluroxypyr-meptyl.

21. The method of claim 19, wherein the ALS inhibiting herbicide is diclosulam.

22. The method of claim 21, wherein fluroxypyr or an agriculturally acceptable ester or salt thereof is applied at an application rate from about 25 g ae/ha to about 560 g ae/ha, and diclosulam is applied at an application rate from about 1 g ai/ha to about 50 g ai/ha.

23. The method of claim 22, wherein fluroxypyr or an agriculturally acceptable ester or salt thereof is applied at an application rate from about 25 g ae/ha to about 200 g ae/ha, and diclosulam is applied at an application rate from about 1.1 g ai/ha to about 25.2 g ai/ha.

24. The method of claim 19, wherein the ALS-inhibiting herbicide is cloransulam or an agriculturally acceptable ester or salt thereof.

25. The method of claim 24, wherein fluroxypyr or an agriculturally acceptable ester or salt thereof is applied at an application rate from about 25 g ae/ha to about 560 g ae/ha, and cloransulam or an agriculturally acceptable ester or salt thereof is applied at an application rate from about 1 g ai/ha to about 50 g ai/ha.

26. The method of claim 25, wherein fluroxypyr or an agriculturally acceptable ester or salt thereof is applied at an application rate from about 25 g ae/ha to about 100 g ae/ha, and cloransulam or an agriculturally acceptable ester or salt thereof is applied at an application rate from about 1.1 g ai/ha to about 8.8 g ai/ha.

27. The method of claim 24, wherein the cloransulam or an agriculturally acceptable ester or salt thereof is cloransulam-methyl.

28. The method of claim 19, wherein the ALS-inhibiting herbicide is chlorimuron or an agriculturally acceptable ester or salt thereof.

29. The method of claim 28, wherein fluroxypyr or an agriculturally acceptable ester or salt thereof is applied at an application rate from about 25 g ae/ha to about 560 g ae/ha, and chlorimuron or an agriculturally acceptable ester or salt thereof is applied at an application rate from about 1 g ai/ha to about 90 g ai/ha.

30. The method of claim 29, wherein fluroxypyr or an agriculturally acceptable ester or salt thereof is applied at an application rate from about 25 g ae/ha to about 100 g ae/ha, and chlorimuron or an agriculturally acceptable ester or salt thereof is applied at an application rate from about 1.1 g ai/ha to about 8.8 g ai/ha.

31. The method of claim 28, wherein the chlorimuron or an agriculturally acceptable ester or salt thereof is chlorimuron-ethyl.

32. The method of claim 19, wherein the ALS-inhibiting herbicide is thifensulfuron or an agriculturally acceptable ester or salt thereof.

33. The method of claim 32, wherein fluroxypyr or an agriculturally acceptable ester or salt thereof is applied at an application rate from about 25 g ae/ha to about 560 g ae/ha, and thifensulfuron or an agriculturally acceptable ester or salt thereof is applied at an application rate from about 0.5 g ai/ha to about 25 g ai/ha.

34. The method of claim 33, wherein fluroxypyr or an agriculturally acceptable ester or salt thereof is applied at an application rate from about 17.5 g ae/ha to about 100 g ae/ha, and thifensulfuron or an agriculturally acceptable ester or salt thereof is applied at an application rate from about 0.6 g ai/ha to about 13 g ai/ha.

35. The method of claim 32, wherein the thifensulfuron or an agriculturally acceptable ester or salt thereof is thifensulfuron-methyl.

36. The method of claim 19, wherein fluroxypyr or an agriculturally acceptable ester or salt thereof and the ALS-inhibiting herbicide are applied post-emergence to the undesirable vegetation or crop.

37. The method of claim 19, wherein fluroxypyr or an agriculturally acceptable ester or salt thereof and the ALS-inhibiting herbicide are applied pre-emergence to the undesirable vegetation or a crop.

38. The method of claim 19, wherein the undesirable vegetation comprises a herbicide resistant or tolerant weed.

39. The method of claim 38, wherein the resistant or tolerant weed is a biotype with resistance or tolerance to single or multiple herbicides or single or multiple chemical classes, or inhibitors of single or multiple herbicide modes-of-action.

40. The method of claim 39, wherein the resistant or tolerant weed is a biotype resistant or tolerant to acetolactate synthase (ALS) or acetohydroxy acid synthase (AHAS) inhibitors, photosystem II inhibitors, acetyl CoA carboxylase (ACCase) inhibitors, photosystem I inhibitors, 5-enolpyruvyl-shikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall or organoarsenicals.

41. The method of claim 19, wherein the undesirable vegetation is controlled in soybean, canola, sunflower, sugarbeet, alfalfa, corn, cotton, wheat, barley, oats, sorghum or rice, a non-crop, perennial crop, fruiting crop, or plantation crop area, comprising contacting undesirable vegetation or the locus thereof in a row crop, drilled crop, fallow-bed, fallow land, non-crop, perennial crop, fruiting crop, or plantation crop area.

42. The method of claim 41, wherein the undesirable vegetation is controlled in a non-crop area and the non-crop area is a pasture, grassland, rangeland, fallow land, fence-row, parking area, tank farm, storage area, right-of-way, utility area, turf, forestry, aquatics, industrial vegetation management (IVM) or fallow-bed.

43. The method of claim 42, wherein the undesirable vegetation is contacted prior to planting a crop.

44. The method of claim 41, wherein the undesirable vegetation is controlled in a perennial crop area and foliage of the perennial crop is not contacted when the undesirable vegetation is contacted.

45. The method of claim 44, wherein the perennial crop is a tree and vine orchard.

46. The method of claim 45, wherein the tree and vine orchard is selected from citrus, grapes, almond, apple, apricot, avocado, beechnut, Brazil nut, butternut, cashew, cherry, chestnut, chinquapin, crab apple, date, feijoa, fig, filbert, hickory nut, kiwi, loquat, macadamia nut, mayhaws, nectarine, olives, peach, pear, pecan, persimmon, pistachio, plum, pomegranates, prune, quince and walnut.

47. The method of claim 41, wherein the undesirable vegetation is controlled in a fruiting crop area and foliage of the fruiting crop is not contacted when the undesirable vegetation is contacted.

48. The method of claim 47, wherein the fruiting crop is selected from blueberries, guava, *papaya*, strawberries, taro, blackberries and raspberries.

49. The method of claim 41, wherein the undesirable vegetation is controlled in the plantation crop area and foliage of a plantation crop is not contacted when the undesirable vegetation is contacted.

50. The method of claim 49, wherein the plantation crop is selected from coffee, cacao, rubber and palm oil.

51. The method of claim 19, further comprising contacting the undesirable vegetation with a herbicidally effective amount of an additional herbicide.

* * * * *